United States Patent
Vetter et al.

[11] Patent Number: 5,269,764
[45] Date of Patent: Dec. 14, 1993

[54] HEMOSTATIC GASKET AND VALVE ASSEMBLY

[75] Inventors: James W. Vetter, Palo Alto; Eric Fraser, Temecula, both of Calif.

[73] Assignee: Devices for Vascular Intervention, Inc., Redwood City, Calif.

[21] Appl. No.: 934,138

[22] Filed: Aug. 21, 1992

[51] Int. Cl.[5] ............................................. A61M 5/178
[52] U.S. Cl. .................................... 604/167; 604/256; 251/149.1
[58] Field of Search ............... 604/167, 169, 164, 256, 604/905, 283; 137/849; 251/149.1

[56] References Cited

U.S. PATENT DOCUMENTS

| | | | |
|---|---|---|---|
| 4,000,739 | 1/1977 | Stevens | 128/214.4 |
| 4,424,833 | 1/1984 | Spector et al. | 137/849 |
| 4,434,810 | 3/1984 | Atkinson | 137/849 |
| 4,436,519 | 3/1984 | O'Neill | 604/175 |
| 4,723,550 | 2/1988 | Bales et al. | 128/344 |
| 4,752,287 | 6/1988 | Kurtz et al. | 604/99 |
| 4,874,377 | 10/1989 | Newgard et al. | 604/167 |
| 4,946,133 | 8/1990 | Johnson et al. | 604/256 |
| 4,950,257 | 8/1990 | Hibbs et al. | 604/265 |
| 4,960,412 | 10/1990 | Fink | 604/167 |
| 5,059,186 | 10/1991 | Yamamoto et al. | 604/167 |
| 5,064,416 | 11/1991 | Newgard et al. | 604/167 |
| 5,114,408 | 5/1992 | Fleischhaker et al. | 604/167 |
| 5,125,903 | 6/1992 | McLaughlin | 604/256 |
| 5,141,498 | 8/1992 | Christian | 604/167 |
| 5,154,701 | 10/1992 | Cheer et al. | 604/167 |
| 5,167,636 | 12/1992 | Clement | 604/167 |
| 5,167,637 | 12/1992 | Okada et al. | 604/167 |

*Primary Examiner*—John G. Weiss
*Attorney, Agent, or Firm*—Townsend and Townsend Khourie and Crew

[57] ABSTRACT

A hemostatic sealing assembly comprises a valve housing and a two-stage hemostatic gasket. The gasket is disposed in an enlarged recess within a shell component of the housing and held in place by a terminal plug. The front and rear faces of the gasket are conically tapered as are the mating surfaces and the housing shell and terminal plug, respectively. In this way, the gasket can be radially compressed to provide a desired degree of both sliding seal and static seal.

19 Claims, 4 Drawing Sheets

HEMOSTATIC GASKET AND VALVE ASSEMBLY

BACKGROUND OF THE INVENTION

1. Field of the Invention

The present invention relates generally to self-sealing gaskets and, more particularly, to valve assemblies comprising gaskets including both an open aperture to provide a sliding seal and a split septum to provide a static seal.

The introduction of medical catheters to a patient generally requires passage of the catheter through the lumen of a previously introduced tube, sheath, guiding catheter, trocar sleeve, or the like. After initial introduction, it is frequently necessary to remove the catheter to perform some task (such as the injection of contrast medium) or to interchange the first catheter with a second. To facilitate such removal and/or interchange, a variety of "hemostatic valves" have been proposed to provide both a sliding seal against the introduced catheter (when it is in place) as well as a static seal (when the catheter has been removed). A typical hemostatic valve will include a gasket having both an open aperture for providing the sliding seal against the introduced catheter and a split septum for providing the static seal when the catheter has been removed.

While generally successful, conventional hemostatic valve designs suffer from certain drawbacks. Present designs often allow excessive blood loss, particularly during manipulation and repositioning of devices, such as guidewires, angioplasty catheters, atherectomy catheters, and the like. Blood loss can be a particular problem in newer "bare wire" atherectomy techniques where frequent repositioning of the device or wire are necessary. Many of the designs are rather complex and difficult to manufacture. Moreover, many of the present hemostatic valve designs are less effective when sealing against a vacuum, (e.g., during aspiration) than when sealing against positive blood pressure. Additionally, the gaskets within the hemostatic valve assemblies can become misaligned and damaged as a result of introducing a catheter therethrough. Such misalignment and damage are particular problems with catheters having rigid housings at their distal ends, such as atherectomy catheters having cutter housings at their distal ends. Such damage to the seal is often evident when leakage occurs through the static seal after the catheter has been removed.

For these reasons, it would be desirable to provide improved hemostatic valves for use with medical devices, such as guiding catheters, introducer sheaths, trocar sleeves, and the like. Such devices should provide an effective hemostatic seal at all times, including during the manipulation and repositioning of devices introduced therethrough. It would be further desirable if such housings and associated gaskets were easy to manufacture and use, and were able to seal against vacuum as well as against positive internal pressure. In particular, such improved hemostatic valves should include gaskets which readily receive a wide variety of catheters and which do not become misaligned and/or damaged as a result of catheter passage therethrough.

2. Description of the Background Art

U.S. Pat. No. 4,723,550, describes a hemostasis valve including an internal gasket having conical face and an axial passage. The passage may be radially constricted about a guide wire by axially compressing the gasket. U.S. Pat. No. 4,428,833, describes a molded, one-piece self-sealing gasket comprising a split-septum spaced-apart from a plug portion. U.S. Pat. No. 4,000,739, describes a hemostasis valve having disc-shaped gasket having a central aperture disposed against a disc-shaped split gasket. Other hemostatic valve structures are described in U.S. Pat. Nos. 4,960,412; 4,950,257; 4,752,287; and 4,436,519.

SUMMARY OF THE INVENTION

A hemostatic sealing assembly for use with medical devices such as guiding catheters, introducer sheaths, trocar sleeves, and the like, comprises a two-stage hemostatic gasket disposed in a valve housing. The gasket comprises a cylindrical body composed of an elastomeric material, where the body has a front conical face, a back conical face, and an axial lumen extending therebetween. A split septum is integrally formed in the body and disposed within the axial lumen generally at the front conical face thereof.

The valve housing encloses the hemostatic gasket and supports the gasket in a manner that enhances its ability to provide both sliding and static seals, as described in more detail below. In particular, the valve housing includes an outer shell having a central passage with an enlarged threaded receptacle at one end of the passage. A connector having a central passage and a threaded shank it is threadably received in the receptacle of the outer shell so that the connector can be axially advanced and retracted relative to the shell by rotation. The receptacle terminates at its interior end in a conical surface which mates with the front conical face of the gasket. The shank of the connector, in turn, terminates in a conical surface which mates with the back conical face of the gasket. In this way, the gasket is held firmly in place at all times and may be axially compressed (by incrementally screwing the connector into the shell) resulting in radial compression against any catheter or other device which may be in the axial lumen of the gasket. Additionally, such radial compression can serve to enhance the static sealing of the split septum when no device is present in the lumen of the gasket.

Such construction of the hemostatic sealing assembly provides certain advantages when compared to previous valve structures. A primary benefit is derived from an enhanced hemostatic seal, both when a device is in place and when the device is being manipulated or repositioned within the valve. In particular, the valve of the present invention provides a "halfway" open position that not only allows manipulation of a device (while still effectively blocking excessive blood loss), but also facilitates air purging by permitting controlled "backbleeding." The design of the static seal further allows continuous hemodynamic monitoring, even during device manipulation. Moreover, the use of opposed conical faces to entrap both the front and back ends of the gasket assures proper alignment when a catheter or other device is being introduced therethrough. Additionally, the opposed conical faces help assure uniform radial compression (along the length of the axial lumen) as the gasket is axially compressed within the housing. This helps improve both the sliding and static seals provided by the gasket. The sliding seal can be effective against even relatively high vacuums which are drawn downstream in the housing. Additionally, both the gasket and the valve housing are relatively easy and inexpensive to manufacture.

DESCRIPTION OF THE SPECIFIC EMBODIMENT

According to the present invention a hemostatic sealing assembly is provided for use with the variety of medical devices which effect percutaneous penetration into a blood vessel, body lumen, hallow body organ, solid tissue, or the like, and where it is desired to introduce a catheter or other apparatus through the proximal end of the device. Exemplary medical devices include guiding catheters, introducer sheaths, trocar sleeves, and the like, where the hemostatic sealing assembly of the present invention will be located at a proximal end of the device (which remains outside the patient) to provide both a sliding seal when the catheter is introduced therethrough and a static seal when the catheter is removed. The hemostatic sealing assembly of the present invention is particularly useful with vascular guiding catheters which are used for introducing interventional catheters, such as atherectomy catheters, angioplasty catheters, imaging catheters, and the like, to desired regions within the patient's vascular system. Such guiding catheters are described in U.S. Pat. No. 4,817,613, and copending application Ser. No. 07/831,599, the disclosures of which are incorporated herein by reference.

The hemostatic sealing assembly of the present invention is particularly useful for introducing atherectomy catheters and other catheters with rigid housing at their distal end. In the case of atherectomy catheters of the type disclosed in U.S. Pat. No. Re. 33,569, the disclosure of which is incorporated herein by reference, the hemostatic seal is subjected to potential damage by the presence of an elongate cutting aperture on the side of the housing, which aperture can damage the seal as it is introduced. As will be described in greater detail hereinafter, the hemostatic sealing assembly of the present invention provides for precise and secure alignment of a two-stage sealing gasket to resist damage from any catheter as it is being introduced.

Figure 1:
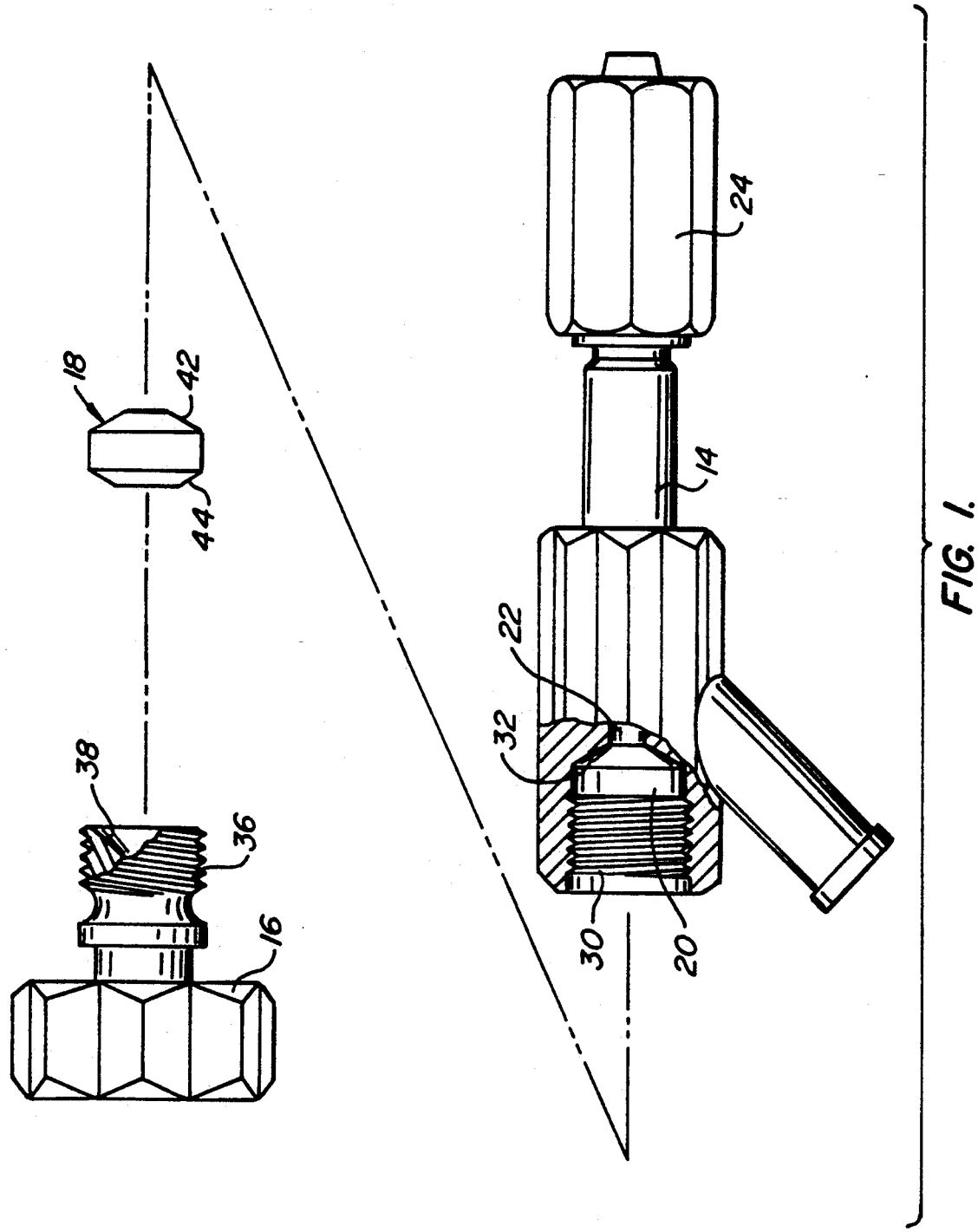
FIG. 1 is an exploded elevational view illustrating the components of a hemostatic sealing assembly constructed in accordance with the principles of the present invention.
Figure 2:
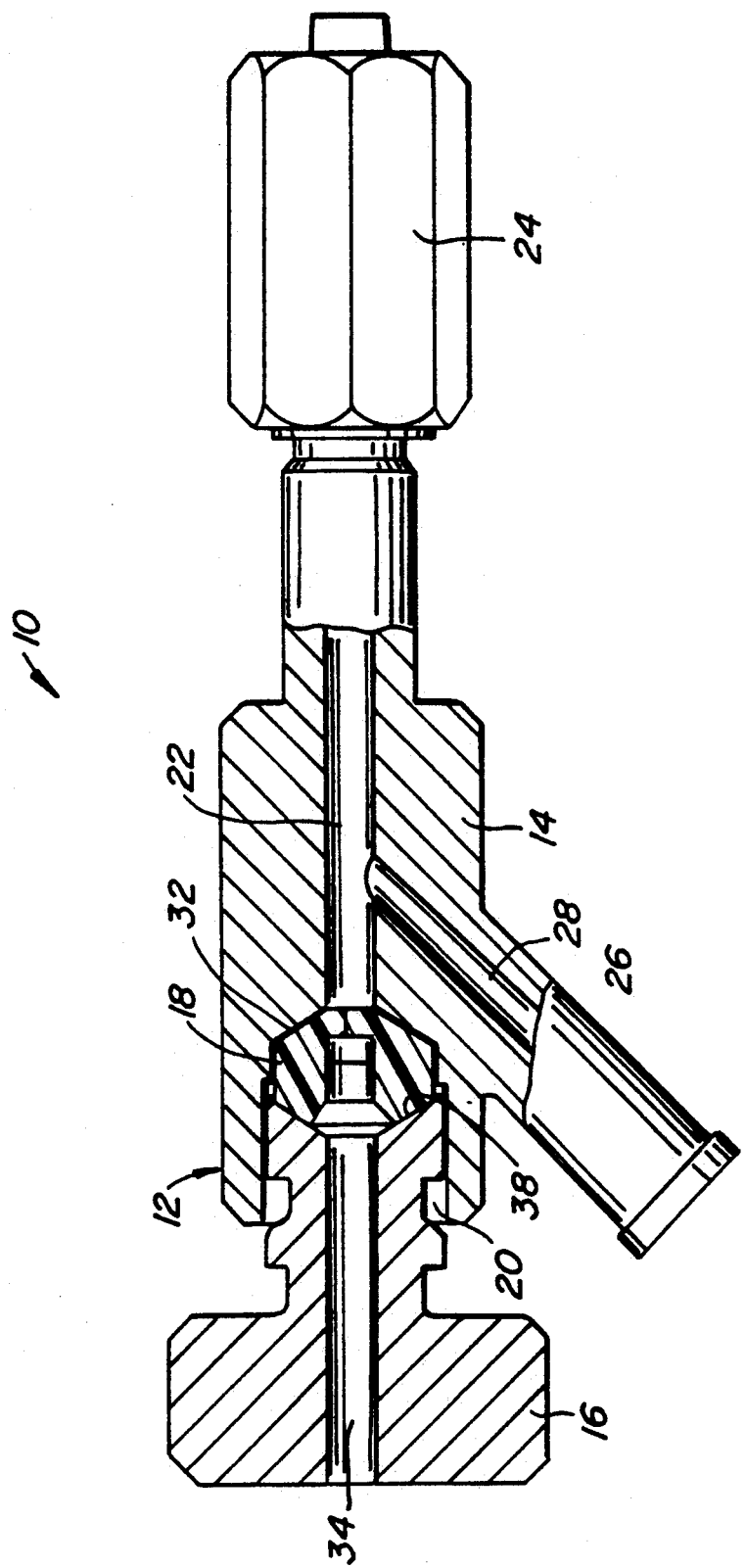
FIG. 2 is a side elevational view of the assembled hemostatic sealing assembly of FIG. 1, shown with portions broken away.

Referring now to FIGS. 1 and 2, a hemostatic sealing assembly 10 constructed in accordance with the principles of the present invention comprises a valve housing 12 which includes an outer shell 14 and a terminal plug 16. The assembly 10 further includes a hemostatic gasket 18 which is entrapped within an enlarged receptacle 20 formed in one end of the housing 14 by the terminal plug 16 (when it is received within the receptacle 20). The housing 14 further includes a central passage 22 which is axially disposed in the housing and which opens into the enlarged recess 20. The housing 14 further includes a standard luer fitting 24 at the end opposite to the enlarged recess 20. In this way, any device entering through the recess 20 into the central passage 22 can pass through and out of the luer fitting 24. It will be appreciated that the luer fitting 24 can be connected to a wide variety of medical devices, such as guiding catheters, introducer sheaths, trocar sleeves, and the like, as is well known in the art.

Housing 14 further includes a branch connector 26 which defines a passage 28 connecting with the central passage 22. In this way, the central passage 22 (and any device which is connected to the luer fitting 24) can be connected to an outside source of perfusion, aspiration, contrast media, or the like.

The enlarged recess 20 has a threaded inside wall 30 and terminates at its inner end in a conical surface 32. The conical surface 32 is concave in nature and adapted to receive a mating surface 42 on the hemostatic sealing gasket 18, as will be described in greater detail hereinafter. The terminal plug 16 also includes a central passage 34 which, when the terminal plug is connected to the housing 14, is generally aligned with central passage 22 of the housing, as best observed in FIG. 2. The plug 16 includes a threaded shank portion 36 which is threadably received within the threaded wall portion of the enlarged receptacle 20. Additionally, the inside of the forward end of the threaded shank 36 is formed as a concave conical surface 38 which is adapted to mate with a corresponding conical surface 44 on the hemostatic gasket 18, as will be described in greater detail hereinafter.

Figure 3:
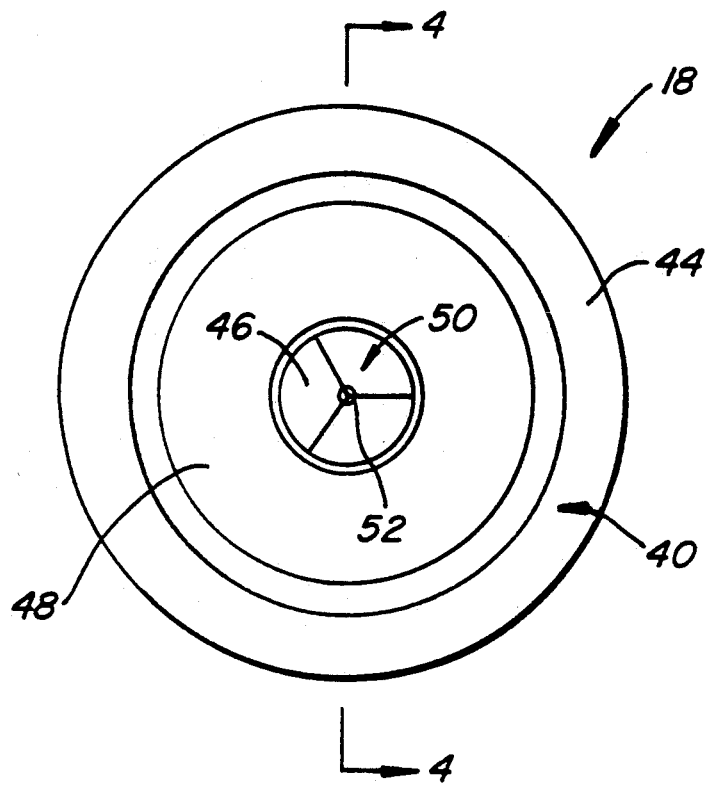
FIG. 3 is a front, elevational view of a hemostatic gasket constructed in accordance with the principles of the present invention.
Figure 4:
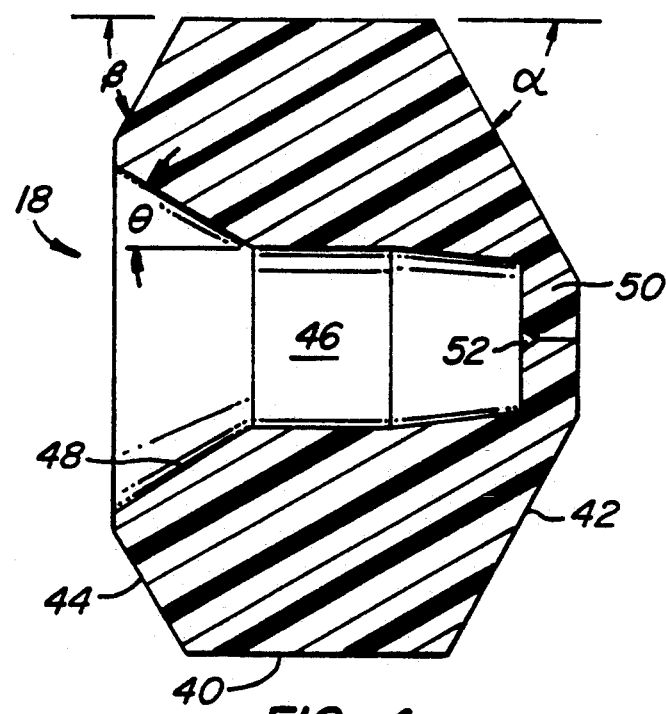
FIG. 4 is a cross-sectional view taken along line 4—4 of FIG. 3.

Referring now in particular to FIGS. 3 and 4, the hemostatic gasket 18 comprises a cylindrical body 40 composed of an elastomeric material, such as silicone rubber, or the like. A particularly suitable material is Dapro Fluorosilicone 8590-30, available from Dapro Rubber, Inc. The cylindrical body 40 will be molded to have the shape illustrated, including a front conical face 42, a back conical face 44, and an axial lumen 46. The front conical face is formed at an angle $\alpha$ relative to the axial direction while the back conical face 44 is formed in an angle $\beta$ relative to the axial direction. While angles $\alpha$ and $\beta$ are not necessarily equal, they frequently will be, and will generally be between 45° and 70°, typically being 60° from axial.

The axial lumen 46 of the gasket 18 will provide a sliding seal when a catheter is introduced to the hemostatic sealing assembly 10, as described in greater detail hereinafter. To facilitate passing the catheter through the axial lumen 46, an enlarged chamfered lip 48 is provided on the back face. The lip will typically be formed at an angle $\theta$ from 20° to 40° relative to the axial direction. A split septum 50 is integrally formed within the front face 42 of hemostatic gasket 18. The septum 50 will usually be split along three radial lines spaced approximately 120° apart, but it would also be possible to employ more splits.

It has been found that the location of a central notch 52 at the central point where all slits meet greatly facilitates opening of the split septum 50 as a catheter is introduced. The notch 52 provides for a thinning effect which helps direct the catheter to be introduced to the center of the septum 50 to lessen the force required to open the septum.

The dimensions of the gasket 18 will be selected to accommodate those of the sealing assembly 10. Typically, the gasket will have an outside diameter of from about 6 mm to 10 mm, usually being about 8 mm; an inside diameter from about 2 mm to 3 mm, usually being from 2.3 mm to 2.9 mm; and a length from about 5 mm to 6 mm. In particular, the axial lumen diameter will be chosen to be slightly larger than the diameter of the catheter to be introduced. In this way, the introduced catheter can be freely advanced and retracted at first, with the gasket 18 later being compressed to enhance the seal after the catheter has been properly positioned.

Referring again to FIGS. 1 and 2, the hemostatic gasket 18 is received between the conical surface 32 of receptacle 30 and the conical surface 38 of the terminal plug 16, with the angles of the conical surfaces 32 and 38 being selected to correspond to the angles on the conical faces 42 and 44 of the gasket. It will be appreciated that the axial compressive forces on the gasket 18 can be increased by screwing the terminal plug 16 further into the receptacle 30, that is simply by turning the plug. By increasing the axial compressive forces on the gasket 18, the conical surfaces 32 and 38 interact with the conical faces 42 and 44 to radially compress the gasket. When no catheter is in place (as illustrated in FIG. 2) the split septum 50 remains closed and inhibits leakage through the gasket 18. This is particularly useful when fluid is being introduced to or withdrawn from the catheter through connector 26. Typically, pressures within the housing up to about 40 psi, and vacuums down to about 38 in Hg can be contained.

Figure 5A:
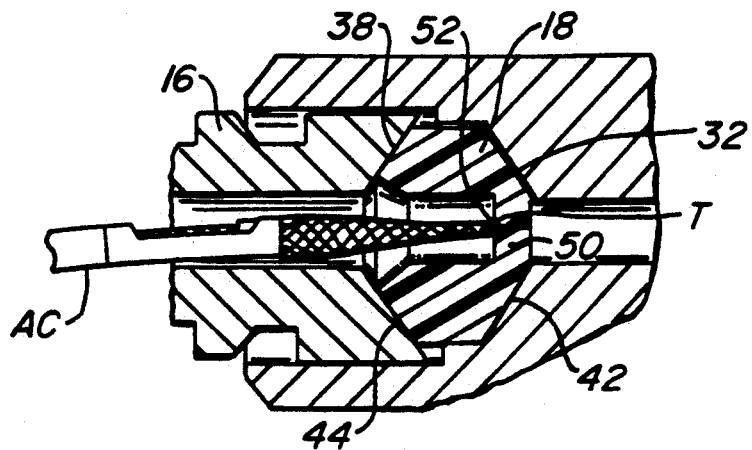
FIGS. 5A-5C illustrate the introduction of an atherectomy catheter through the hemostatic sealing assembly of the present invention.
Figure 5B:
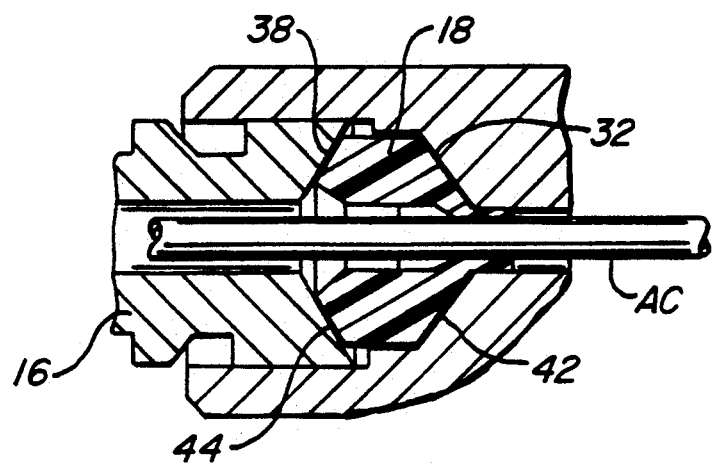
Figure 5C:
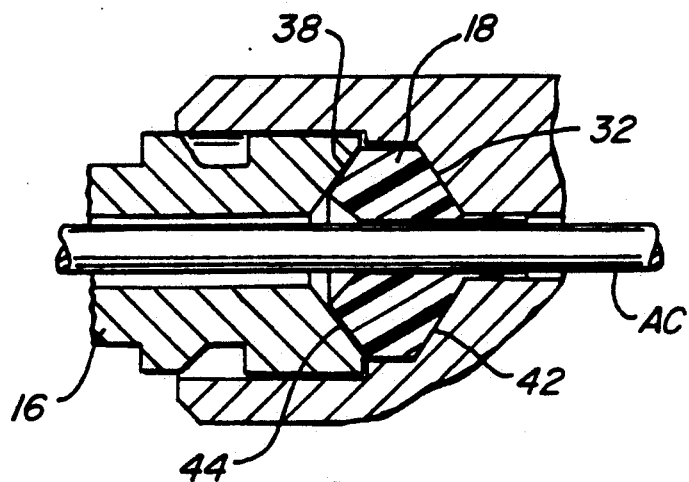

Referring now to FIGS. 5A–5C, introduction of an atherectomy catheter AC through the sealing apparatus 10 will be described. It will be appreciated that, prior to introducing the atherectomy catheter AC, the hemostatic sealing apparatus 10 will have been connected to a guiding catheter (not illustrated) which has been properly positioned within a patient's vascular system.

When the atherectomy catheter AC is first introduced, the hemostatic gasket 18 will typically be under only moderate compressive forces. The opposed conical surfaces 32 and 38 will, however, act to maintain the proper alignment of the gasket 18 by mating against the conical faces 42 and 44. The distal tip T of the atherectomy catheter is introduced so that it engages the notch 52 and the split septum 50. Such engagement will occur naturally as the catheter tip T seeks out the thinned region within the septum 50.

After passing the catheter tip T through the septum 50, the catheter body passes through the separated flaps of the septum, as illustrated in FIG. 5B. At this point, there will be a reasonable sliding seal formed between the exterior of the catheter AC and the interior surface of the gasket 18. The sliding seal, however, may not be sufficient to inhibit loss of blood to a desired level. In that case, it will be possible to tighten the terminal plug 16 by rotating the plug so that it advances in a forward direction (to the right as illustrated in FIGS. 5A–5C). As illustrated in FIG. 5C, such tightening causes the radial compression of the hemostatic gasket, closing the axial lumen more tightly about the exterior of the catheter AC. In particular, the compression will be very uniform along the length of the axial lumen so that maximum sealing is achieved with minimum drag on the catheter. That is, it will be possible to provide a desired level of sliding seal, while permitting desired degree of free movement of the catheter through the gasket 18.

Although the foregoing invention has been described in detail for purposes of clarity of understanding, it will be obvious that certain modifications may be practiced within the scope of the appended claims.

What is claimed is:

1. A two-stage hemostatic gasket comprising a cylindrical body composed of an elastomeric material, said body having a front conical face, a back conical face, and an axial lumen extending therebetween, wherein a split septum is integrally formed in the axial lumen within the front conical face, said split septum defining axially-deflectable flaps extending across said axial lumen, said flaps configured to deflect outside said axial lumen when engaged by a catheter passing therethrough.

2. A gasket as in claim 1, wherein the back conical face further includes a chamfered lip about the lumen for aligning a catheter passing therethrough.

3. A gasket as in claim 1, wherein a notch is formed at the center of the split septum to facilitate passage of a catheter therethrough.

4. A gasket as in claim 1, wherein the front face and back face are conically tapered at angles in the range from about 45° to 75° relative to the axial direction.

5. A gasket as in claim 2, wherein the lip is chamfered at an angle in the range from about 20° to 40° relative to the axial direction.

6. A gasket as in claim 1, wherein the gasket is formed from silicone rubber.

7. A hemostatic sealing assembly comprising:
a two-stage hemostatic gasket comprising a cylindrical body composed of an elastomeric material, said body having a front conical face, a back conical face, and an axial lumen extending therebetween, wherein a split septum is integrally formed in the axial lumen within the front conical face, said split septum defining axially-deflectable flaps extending across said axial lumen, said flaps configured to deflect outside said axial lumen when engaged by a catheter passing therethrough; and
a valve housing including (1) an outer shell having a central passage with an enlarged threaded receptacle at one end thereof and (2) a connector having a central passage and a threaded shank which is received in the receptacle, wherein the receptacle provides a conical surface to mate with the front conical face of the gasket and the connector provides a conical surface to mate with the back conical surface of the gasket, whereby the gasket can be entrapped in the receptacle with sealing forces being adjusted by axially positioning the connector.

8. A hemostatic sealing assembly as in claim 7, wherein the housing further includes a luer fitting on the outer shell thereof.

9. A hemostatic sealing assembly as in claim 7, wherein the housing further includes a branch connector open to the central passage.

10. A hemostatic sealing assembly as in claim 7, wherein the back conical face of the gasket further includes a chamfered lip about the lumen for aligning a catheter passing therethrough.

11. A hemostatic sealing assembly as in claim 7, wherein a notch is formed in the center of the split septum of the gasket to facilitate passage of a catheter therethrough.

12. A hemostatic sealing assembly as in claim 7, wherein the front face and back face of the gasket are conically tapered at angles in the range from about 45° to 75° relative to the axial direction.

13. A hemostatic sealing assembly as in claim 10, wherein the lip of the gasket is chamfered at an angle in the range from about 20° to 40° relative to the axial direction.

14. A hemostatic sealing assembly as in claim 10, wherein the gasket is formed from silicone rubber.

15. A two-stage hemostatic gasket comprising a cylindrical body composed of an elastomeric material, said body having a front conical face, a back conical face, and an axial lumen extending therebetween, wherein a split septum is integrally formed in the axial lumen within the front conical face, and wherein the back conical face further includes a chamfered lip about the lumen for aligning a catheter passing therethrough.

16. A gasket as in claim 15, wherein the lip is chamfered at an angle in the range from about 20° to 40° relative to the axial direction.

17. A hemostatic sealing assembly comprising:
a two-stage hemostatic gasket comprising a cylindrical body composed of an elastomeric material, said body having a front conical face, a back conical face, and an axial lumen extending therebetween, wherein a split septum is integrally formed in the axial lumen within the front conical face, and wherein the back conical face of the gasket further includes a chamfered lip about the lumen for aligning a catheter passing therethrough; and
a valve housing including (1) an outer shell having a central passage with an enlarged threaded receptacle at one end thereof and (2) a connector having a central passage and a threaded shank which is received in the receptacle, wherein the receptacle provides a conical surface to mate with the front conical face of the gasket and the connector provides a conical surface to mate with the back conical surface of the gasket, whereby the gasket can be entrapped in the receptacle with sealing forces being adjusted by axially positioning the connector.

18. A hemostatic sealing assembly as in claim 17, wherein the lip of the gasket is chamfered at an angle in the range from about 20° to 40° relative to the axial direction.

19. A hemostatic sealing assembly as in claim 17, wherein the gasket is formed from silicone rubber.

* * * * *